(12) United States Patent
Nakamura et al.

(10) Patent No.: US 7,488,581 B2
(45) Date of Patent: Feb. 10, 2009

(54) METHOD FOR DETECTING A TARGET NUCLEIC ACID SEQUENCE

(75) Inventors: Naoko Nakamura, Kawasaki (JP); Koji Hashimoto, Atsugi (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 11/378,453

(22) Filed: Mar. 20, 2006

(65) Prior Publication Data

US 2007/0218464 A1 Sep. 20, 2007

(51) Int. Cl.
- *C12Q 1/68* (2006.01)
- *C07H 21/02* (2006.01)
- *C07H 21/04* (2006.01)

(52) U.S. Cl. .......................... 435/6; 536/24.3; 536/23.1

(58) Field of Classification Search ............ 435/6, 435/91.2; 536/23.1, 24.3
See application file for complete search history.

(56) References Cited

U.S. PATENT DOCUMENTS

| | | | |
|---|---|---|---|
| 5,776,672 A | | 7/1998 | Hashimoto et al. |
| 5,925,517 A | * | 7/1999 | Tyagi et al. ............ 435/6 |
| 5,972,692 A | | 10/1999 | Hashimoto et al. |
| 6,410,278 B1 | * | 6/2002 | Notomi et al. .......... 435/91.2 |
| 6,667,155 B2 | * | 12/2003 | Hijikata et al. .......... 435/6 |
| 7,081,527 B2 | * | 7/2006 | Cunningham et al. ..... 536/23.1 |
| 2002/0164614 A1 | * | 11/2002 | Becker ................ 435/6 |
| 2006/0003325 A1 | * | 1/2006 | Nakayama ............. 435/6 |
| 2007/0218464 A1 | | 9/2007 | Nakamura et al. |

FOREIGN PATENT DOCUMENTS

| | | |
|---|---|---|
| JP | 05-199898 | 8/1993 |
| JP | 5-199898 | 8/1993 |
| JP | 2001-103981 | 4/2001 |
| JP | 2002-125695 | 5/2002 |
| JP | 3313358 | 5/2002 |
| JP | 2002-186481 | 7/2002 |
| JP | 2002-272475 | 9/2002 |
| JP | 2002-272475 A | 9/2002 |
| JP | 2002-345499 | 12/2002 |
| JP | 2002-355083 A | 12/2002 |
| JP | 2003-159100 | 6/2003 |
| JP | 2003-159100 A | 6/2003 |
| JP | 2003-174900 | 6/2003 |
| JP | 2005-143492 | * 6/2005 |
| WO | 00/28082 | 5/2000 |

OTHER PUBLICATIONS

Notomi et al. Loop-mediated isothermal amplification of DNA. Nucleic Acids Research 28(18) : e63, I-vii (2000).*
Matthews et al., Review : Analytical Strategies for the use of DNA probes. Analytical Biochemistry 169 : 1-25 (1988).*
Tyagi et al., Molecular Beacons : Probes that fluoresce upon hybridization. Nature Biotechnology 14 : 303-308 (1996).*
Ann Cavaiani Pease, et al., "Light-generated oligonucleotide arrays for rapid DNA sequence analysis," Proc. Natl. Acad. Sci. USA, vol. 91, pp. 5022-5026, May 1994.
U.S. Appl. No. 12/014,592, filed Jan. 15, 2008, Nakamura et al.
U.S. Appl. No. 12/015,645, filed Jan. 17, 2008, Nakamura et al.
Nagamine, et al. "Isolation of Single-Stranded DNA from Loop-Mediated Isothermal Amplification Products", Biochemical and Biophysical Research Communications, vol. 290, 2002, pp. 1195-1198.
Trends in Biotechnology, 2002, vol. 20, No. 5, pp. 189-190.

\* cited by examiner

*Primary Examiner*—Ethan Whisenant
(74) *Attorney, Agent, or Firm*—Oblon, Spivak, McClelland, Maier & Neustadt, P.C.

(57) ABSTRACT

A method of detecting a target nucleic acid sequence comprising providing a stem-and-loop structured nucleic acid for measurement wherein the nucleic acid comprises complementary sequence portions located at both terminals and a target sequence portion therebetween as well as a double-stranded portion formed by hybridization of the complementary sequence portions located at both terminals and a remaining looped single-stranded portion, providing a probe nucleic acid having a sequence complementary to the target sequence portion wherein one end of the probe nucleic acid being immobilized to a solid substrate surface, reacting the nucleic acid for measurement with the probe nucleic acid to specifically hybridize the target sequence portion of the nucleic acid for measurement to the probe nucleic acid, and detecting presence or absence of the nucleic acid for measurement hybridized to the probe nucleic acid.

14 Claims, 14 Drawing Sheets

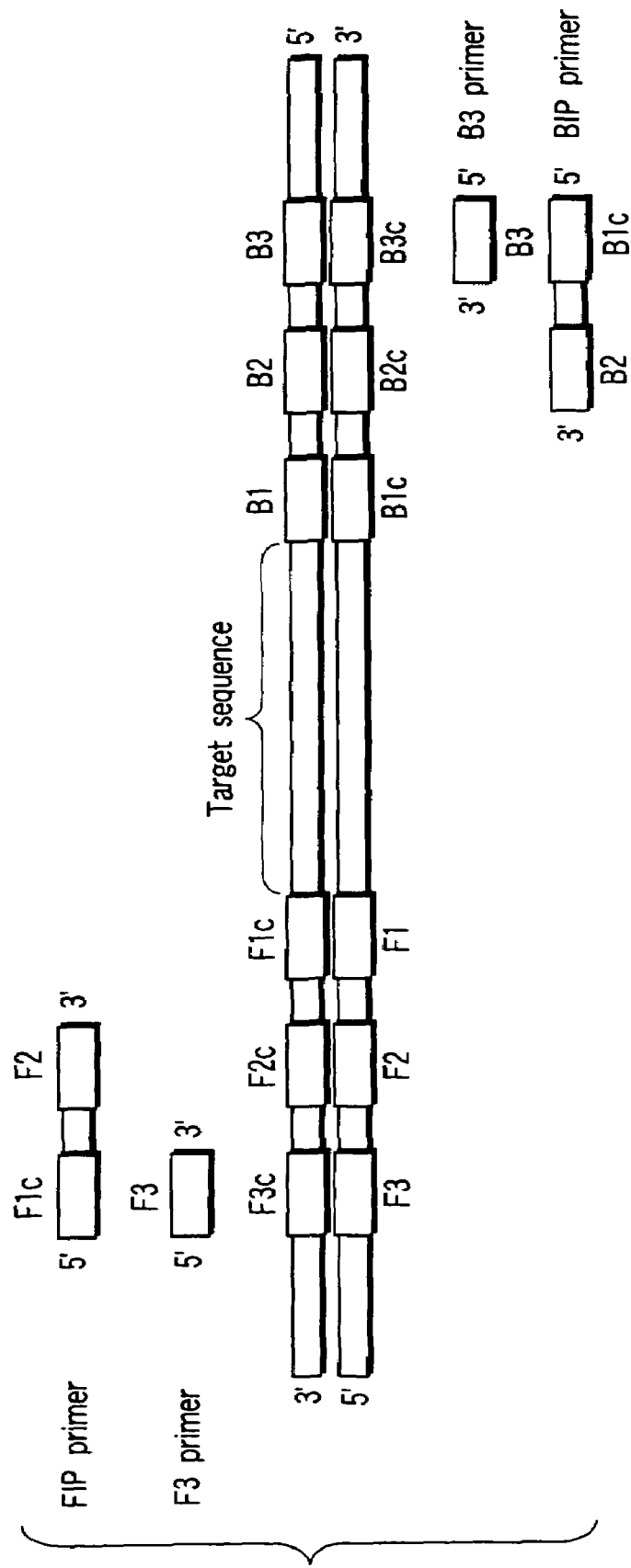
F I G. 1

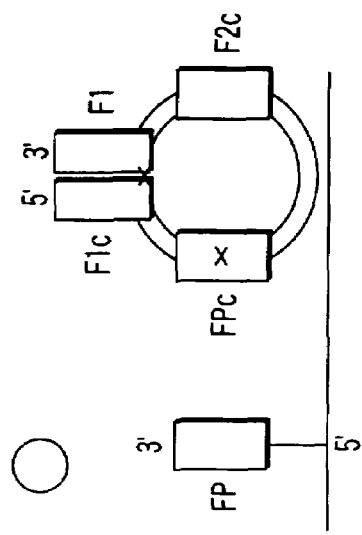
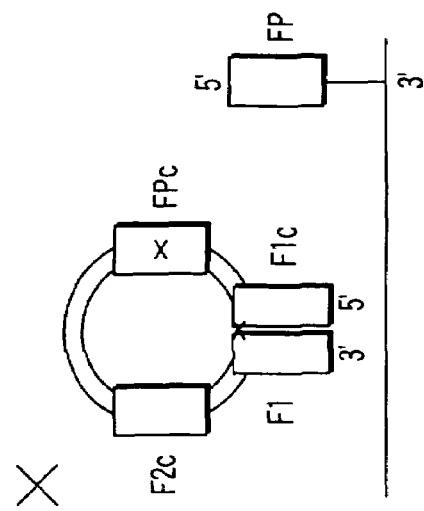
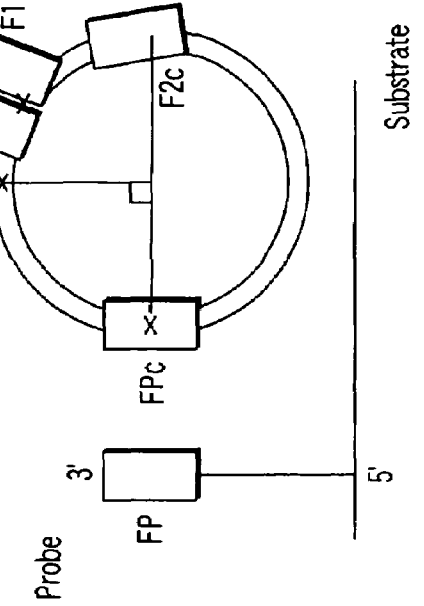
FIG. 5B
FIG. 5C
FIG. 5A

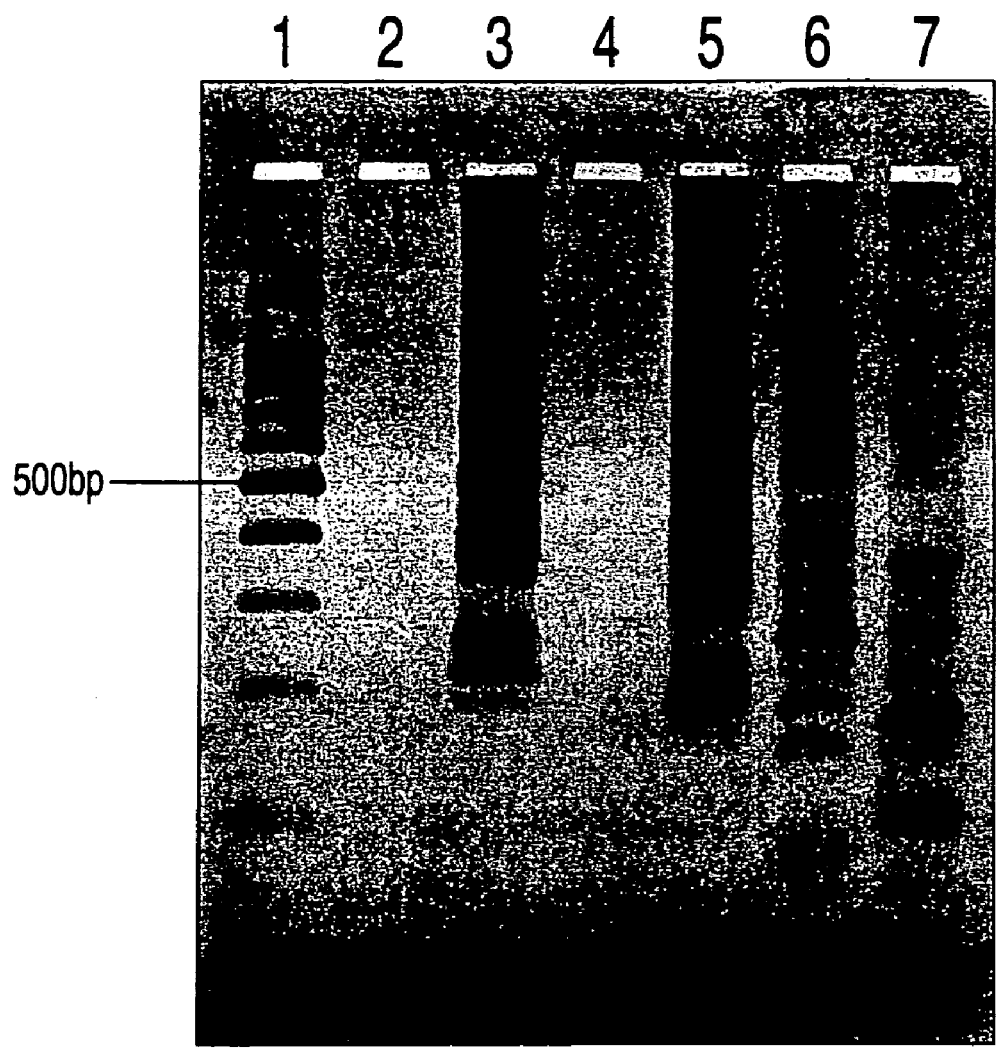
F I G. 9

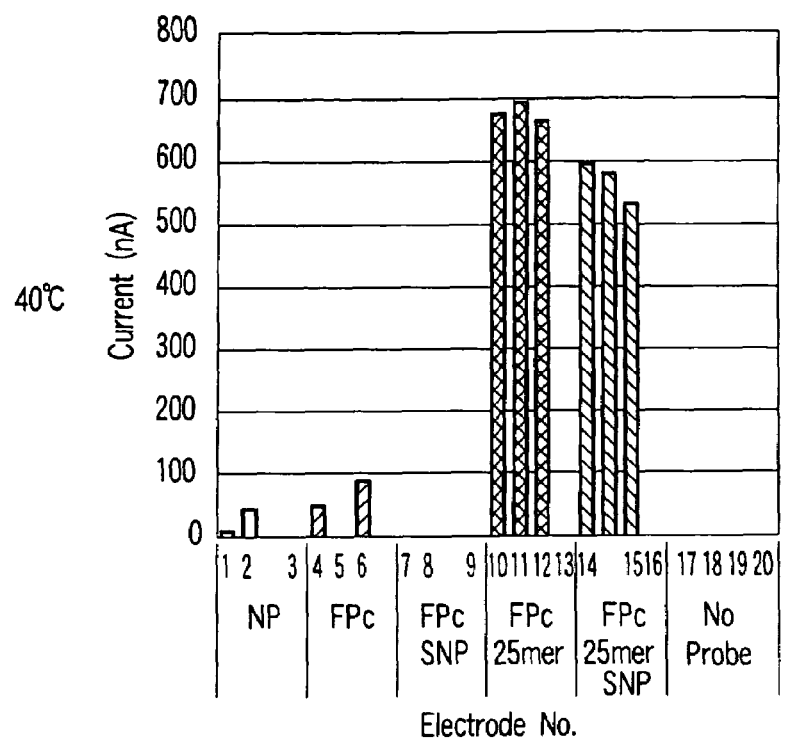
F I G. 13C
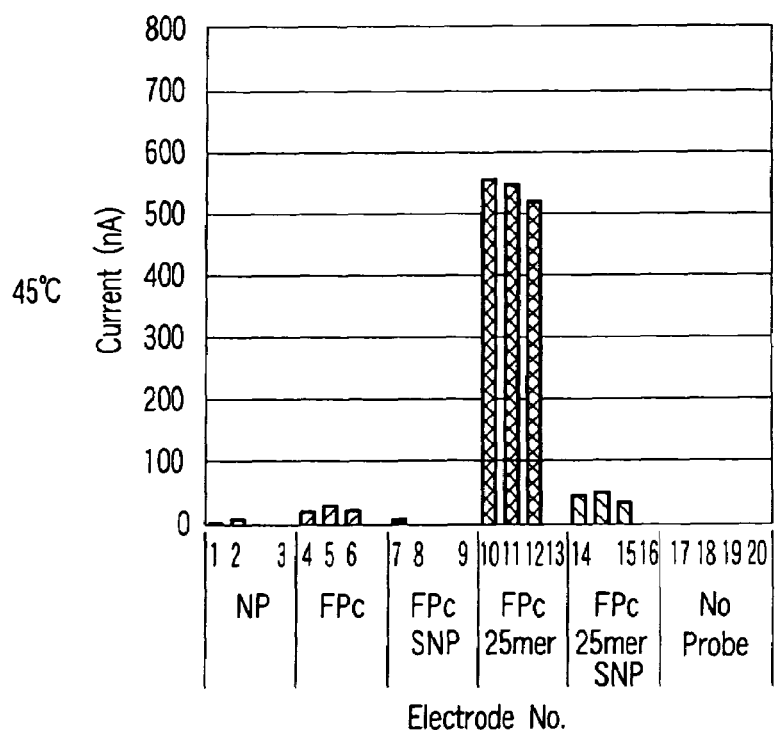
F I G. 13D

SEQUENCE LISTING

```
<160> NUMBER OF SEQ ID NOS: 15

<210> SEQ ID NO 1
<211> LENGTH: 22
<212> TYPE: DNA
<213> ORGANISM: Homo sapiens

<400> SEQUENCE: 1
acagaagaga gaggaatctg gt                                              22

<210> SEQ ID NO 2
<211> LENGTH: 48
<212> TYPE: DNA
<213> ORGANISM: Homo sapiens

<400> SEQUENCE: 2
tgtttcttct ttggcaggag atgagaagga ccaaatcagg agagagca                  48
```

-continued

<210> SEQ ID NO 3
<211> LENGTH: 21
<212> TYPE: DNA
<213> ORGANISM: Homo sapiens

<400> SEQUENCE: 3
gatgaagccc accaaacagt a                                            21

<210> SEQ ID NO 4
<211> LENGTH: 40
<212> TYPE: DNA
<213> ORGANISM: Homo sapiens

<400> SEQUENCE: 4
atgaatacat acagacgtct ccctggggtc tgcaaggaac                        40

<210> SEQ ID NO 5
<211> LENGTH: 27
<212> TYPE: DNA
<213> ORGANISM: Homo sapiens

<400> SEQUENCE: 5
acaaacaaag aatttcttaa ttctcat                                      27

<210> SEQ ID NO 6
<211> LENGTH: 55
<212> TYPE: DNA
<213> ORGANISM: Homo sapiens

<400> SEQUENCE: 6
cgtctgcagg tatgtattca tagactcaaa aaatatactt atttacgctt gaacc       55

<210> SEQ ID NO 7
<211> LENGTH: 21
<212> TYPE: DNA
<213> ORGANISM: Homo sapiens

<400> SEQUENCE: 7
cgaccagatc tgtattgtct t                                            21

<210> SEQ ID NO 8
<211> LENGTH: 50
<212> TYPE: DNA
<213> ORGANISM: Homo sapiens

<400> SEQUENCE: 8
ataaccacat cattttgttc cttgcatgaa ttttctatag gtgaggatga             50

<210> SEQ ID NO 9
<211> LENGTH: 15
<212> TYPE: DNA
<213> ORGANISM: Homo sapiens

<400> SEQUENCE: 9
aacctcgaac aattg                                                   15

<210> SEQ ID NO 10
<211> LENGTH: 15
<212> TYPE: DNA
<213> ORGANISM: Homo sapiens

<400> SEQUENCE: 10

```
caattgttcg aggtt                                                            15

<210> SEQ ID NO 11
<211> LENGTH: 15
<212> TYPE: DNA
<213> ORGANISM: Homo sapiens

<400> SEQUENCE: 11
ctggacgaag actga                                                            15

<210> SEQ ID NO 12
<211> LENGTH: 15
<212> TYPE: DNA
<213> ORGANISM: Homo sapiens

<400> SEQUENCE: 12
caattgttgg aggtt                                                            15

<210> SEQ ID NO 13
<211> LENGTH: 25
<212> TYPE: DNA
<213> ORGANISM: Homo sapiens

<400> SEQUENCE: 13
atcttcaatt gttcgaggtt caagc                                                 25

<210> SEQ ID NO 14
<211> LENGTH: 25
<212> TYPE: DNA
<213> ORGANISM: Homo sapiens

<400> SEQUENCE: 14
atcttcaatt gttggaggtt caagc                                                 25

<210> SEQ ID NO 15
<211> LENGTH: 400
<212> TYPE: DNA
<213> ORGANISM: Homo sapiens

<400> SEQUENCE: 15
ctctagaatt aatttctggg aaggatcagc ctcaggtgcc ttgcattttc tgcttgacag           60
aagagagagg aatctggtac ctggaccaaa tcaggagaga gcagtatatt acaaacaaag          120
aatttcttaa ttctcatctc ctgccaaaga agaaacacca aaaatatac ttatttacgc           180 ttgaacctcg aacaattgaa gattttgagt ctatgaatac ataccctgcag acgtctccaa         240 catcttcatt tataaccaca tcattttgtt ccttgcagac cccagaaggg gtttactgtt         300
tggtgggctt catcctcacc tatagaaaat tcaattataa agacaataca gatctggtcg         360
agtttaaaac tctcactgag gaagaggttg aagaagtgct                                400
```

METHOD FOR DETECTING A TARGET NUCLEIC ACID SEQUENCE

BACKGROUND OF THE INVENTION

1. Field of the Invention

The present invention relates to a technique for detecting a target nucleic acid, more particularly to a method for detecting a target nucleic acid sequence present in a LAMP amplified product and a LAMP amplified product for use in detection of a target nucleic acid.

2. Description of the Related Art

To select correct therapeutic agents, it is important to identify bacteria causing a given infection. Currently, culture method and nucleic acid amplification method are used for microorganism tests.

Recently, improvement in culture method has been made in an effort to improve detection sensitivity and to reduce days of culture. Immunochromatography utilizing antigen-antibody reactions rapidly becomes popular as a simple identification method (see, for example, Japanese Patent Publication No. 2001-103981 (paragraph 0011-0012) and Japanese Patent Publication No. 2002-125695 (paragraph 0002)). However, since this method still takes several weeks for bacterial growth, it hardly meets the needs sought in clinical settings. Consequently, patients are often given a wrong treatment until identification results are obtained.

In contrast, the nucleic acid amplification method uses specific primers to identify bacterial species or resistant bacteria by investigating presence or absence of amplification. This method, including a sample preparation step, can provide test results within approximately 6-7 hours, making it a very useful rapid test. Furthermore, under the recent genomic analysis competition, entire genetic information of many organisms are being analyzed, and as a result, this method is expected to become available for identification of a wide range of bacterial species.

A method well-known as a nucleic acid amplification technique is PCR method (Polymerase Chain Reaction method, Roche). PCR method is widely used as a tool for genetic analyses such as gene cloning and structural determination. However, PCR method has a disadvantage of requiring a complex temperature control device like Thermal Cycler and reaction time over two hours. In PCR method, If synthesis of wrong complementary chains occurs by any chance, the resultant products work as templates for amplification, thereby leading to a wrong identification. In fact, it is difficult to regulate specific amplification based on a difference of only one base in a primer terminal.

In addition, due to the fact that double-stranded products are generated in general when target gene products amplified by PCR method are detected by a DNA chip, complementary strands work as competitors for probes upon a hybridization reaction with the probes, reducing hybridization efficiency and detection sensitivity. To address this problem, such methods as digesting or separating complementary strands have been employed to turn a target into a single-stranded sequence. However, this method has still several problems including a need to use enzymes, expensiveness due to the use of magnetic beads, and handling complexity.

LAMP method (Loop-mediated isothermal amplification method) has been developed as a gene amplification method to fix this problem. LAMP method completes gene amplification within one hour under an isothermal condition. Also, 100-1,000 times amount of final products are obtained compared to that of PCR products. LAMP method also has an advantage of higher specificity as compared to PCR method because six primer regions are set in LAMP method (see, for example, U.S. Pat. No. 3,313,358). LAMP method is expected to be a promising technique to rapidly detect bacteria, viruses and gene mutations (see, for example, Japanese Patent Publication No. 2003-159100) with high sensitivity.

Among tests using LAMP method, a method is now commercialized which detects presence or absence of gene amplification by measuring white turbidity of magnesium pyrophosphate, a by-product which is produced in the course of amplification (see, for example, Japanese Patent Publication No. 2003-174900). In this method where white turbidity of a by-product (magnesium pyrophosphate) is measured, there is no way of confirming whether amplification of an unintended product occurs or not. LAMP method has also a problem that it cannot detect multiple target genes simultaneously.

In addition, methods using intercalators or optical properties have been known as procedures for detecting LAMP amplified products (see, for example, Japanese Patent Publication No. 2002-186481). Other known methods are those measuring degree of fluorescence polarization of reaction solution by fluorescently labeling a probe which hybridizes to a single-stranded loop portion present in a LAMP product (see, for example, Japanese Patent Publication 2002-272475) as well as those immobilizing an insoluble carrier to a 5' terminal side of a primer which hybridizes to a single-stranded loop portion and observing an aggregation reaction associated with amplification reaction (see, for example, Japanese Patent Publication 2002-345499).

BRIEF SUMMARY OF THE INVENTION

According to embodiments of the present invention, there is provided a method of detecting a target nucleic acid sequence comprising:

providing a stem-and-loop structured nucleic acid for measurement wherein the nucleic acid comprises complementary sequence portions located at both terminals and a target sequence portion therebetween as well as a double-stranded portion formed by hybridization of the complementary sequence portions located at both terminals and a remaining looped single-stranded portion;

providing a probe nucleic acid having a sequence complementary to the target sequence portion wherein one end of the probe nucleic acid being immobilized to a solid substrate surface;

reacting the nucleic acid for measurement with the probe nucleic acid to specifically hybridize the target sequence portion of the nucleic acid for measurement to the probe nucleic acid; and detecting presence or absence of the nucleic acid for measurement hybridized to the probe nucleic acid.

BRIEF DESCRIPTION OF THE SEVERAL VIEWS OF THE DRAWING

FIG. 1 is a schematic diagram illustrating an amplification method using a conventional LAMP method.

FIG. 5 schematically illustrates hybridization reaction between nucleic acid probe and a LAMP product in which a target sequence is located in its looped single stranded portion and a nucleic acid probe. In FIGS. 5A and 5B, 5' to 3' sequence orientation of both the nucleic acid probe and the target sequence portion are arranged in a manner where the double-stranded portion in the LAMP product extends away from the substrate plate. In contrast, in FIG. 5C, the 5' to 3' sequence orientation is arranged in a manner where the double stranded portion extends toward the substrate plate.

FIG. 9 is an electrophoresis of LAMP amplification products designed to have a target nucleic acid in a double-stranded region (stem region) or a single-stranded region (loop region) and an electrophoresis of products treated by restriction enzymes.

FIG. 11 is graphs showing measurement results of electrical detection of LAMP products performed in the Example.

FIG. 13 is graphs showing measurement results of electrical detection of SNPs in LAMP products performed in the Example 2. FIG. 13C is a graph showing measurement results obtained from substrate plates immersed in washing buffer at 40° C. for 40 minutes after hybridization. FIG. 13D is a graph showing measurement results obtained from substrate plates immersed in washing buffer at 45° C. for 40 minutes after hybridization.

DETAILED DESCRIPTION OF THE INVENTION

Embodiments of the present invention will now be described in more detail.

<Nucleic Acids for Measurement>

Figure 2:
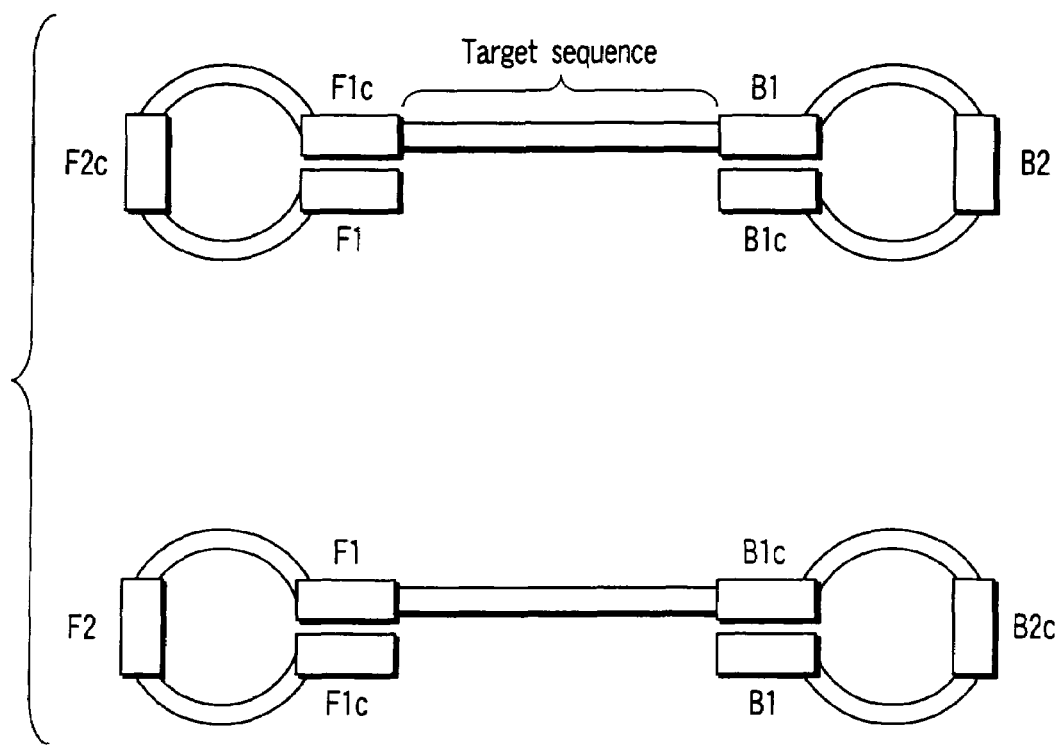
FIG. 2 is a schematic diagram illustrating an amplification product obtained by a conventional LAMP method.

Now, primer designing in LAMP method and intermediate products serving as origins of amplification will be described with reference to FIG. 1 and FIG. 2. In LAMP method, six primer regions will be set and four primers are used for gene amplification. FIG. 1 illustrates double-stranded DNA to be detected. Three regions, F3 region, F2 region and F1 region, in order of proximity to 5' terminal of the double strand, will be determined and three regions, B3c region, B2c region and B1c region, in order of proximity to 3' terminal, will be determined. In addition, F3 region, F2 region and B1 region in complementary strand thereof are called F3c region, F2c region and F1c region, and B3c region, B2c region and B1c regions in complementary strand thereof are called B3 region, B2 region and B1 region, respectively. The six regions, F3 region, F2 region, F1 region, B3c region, B2c region, B1c region and complementary strands regions thereto are hereinafter designated as a primer designing region. Primers constituting four basic primers are FIP primer that has a same sequence with the F2 region at its 3' terminal and a sequence complementary to the F1 region at its 5' terminal, F3 primer comprised of a same sequence with the F3 region, BIP primer having a sequence complementary to B2c region at its 3' terminal and a same sequence with the B1c region at its 5' terminal, and B3 primer comprised of a sequence complementary to the B3c region. LAMP amplification using the four primers described above will cause formation of a dumbbell-shaped intermediate product having a stem-and-loop structure as shown in FIG. 2. Having sequences complementary to each other in the same nucleic acid strand, both terminal portions of the intermediate product will self-anneal and form a single-stranded loop. Intermediate product generation and subsequent amplification process have been well known and are described in detail in Japanese Patent 3,313,358 and Japanese Patent Publication 2002-186481. Traditionally, in LAMP amplification products, target sequences are interposed between B1 and F1c or between F1 and B1c.

Figure 3:
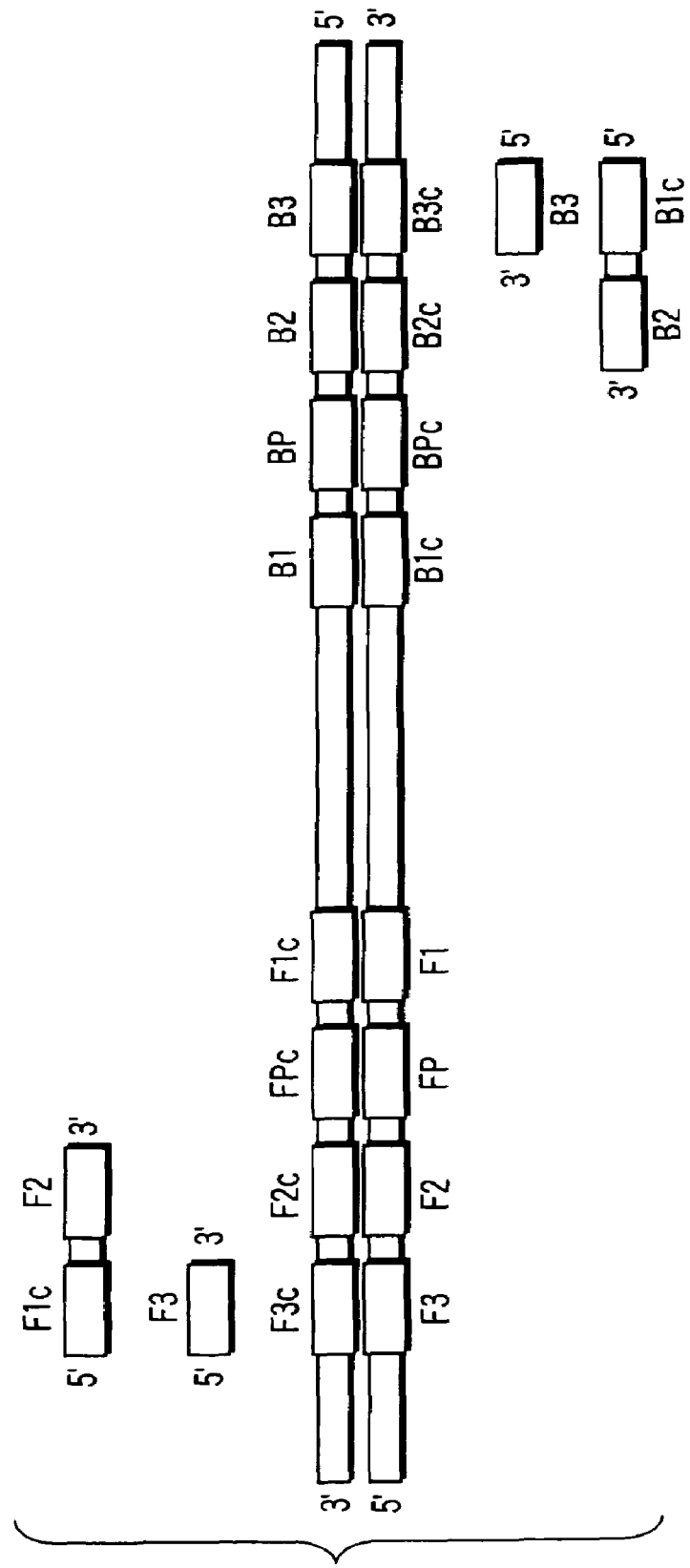
FIG. 3 is a schematic diagram illustrating an amplification method used for production of the nucleic acid for measurement according to an embodiment of the present invention.
Figure 4:
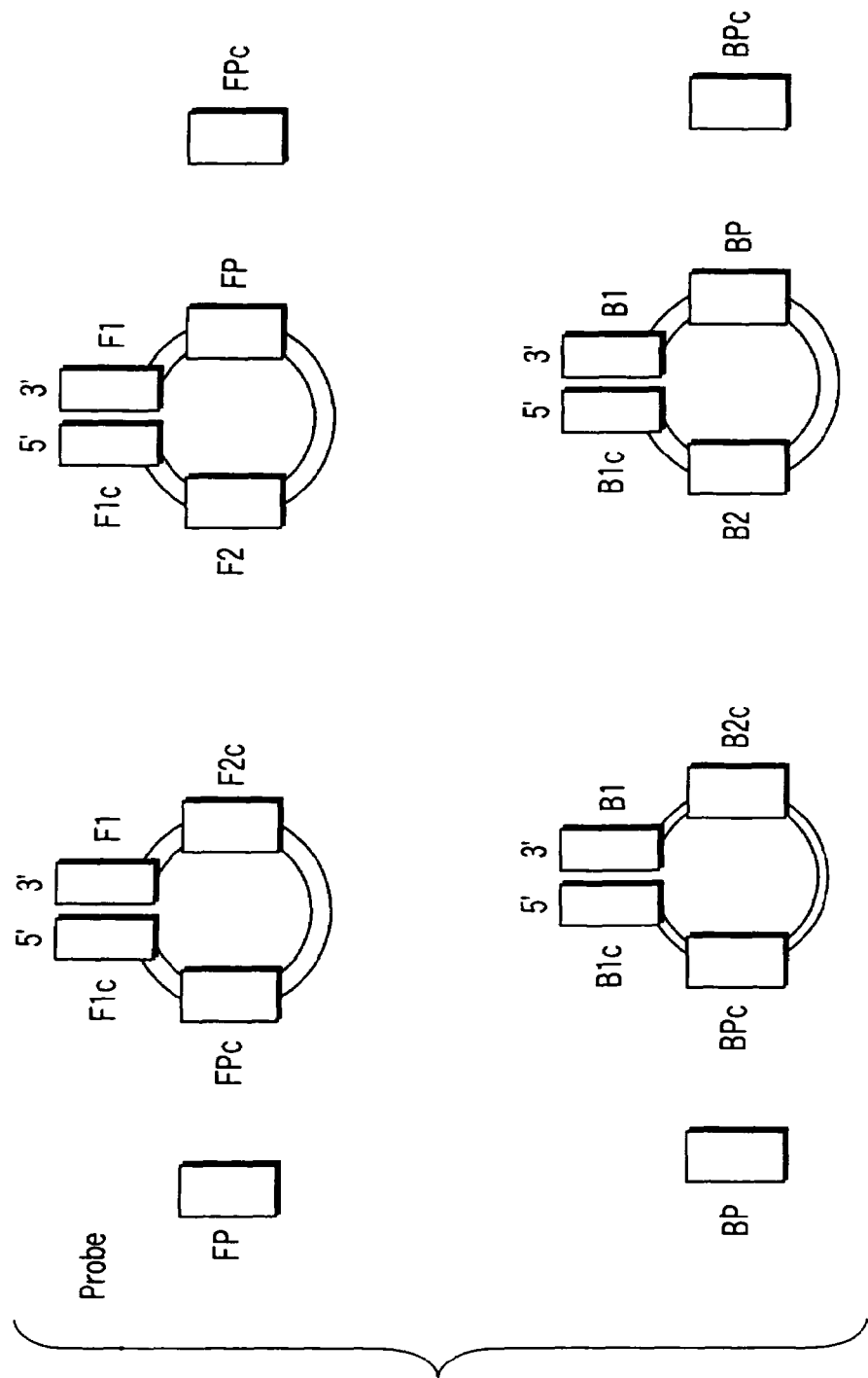
FIG. 4 is a schematic diagram illustrating the nucleic acid for measurement according to an embodiment of the present invention.

In contrast to traditional target sequences shown in FIG. 1 and FIG. 2, primers used in this invention are designed to have target sequences located in the single-stranded loop portion. Accordingly, in this invention, target sequence regions are designed to be located either between primer regions F1c and F2c, primer regions F2 and F1, primers B1c and B2c or primer regions B2 and B1 as shown in FIG. 3. These regions are designated as FPc region, FP region, BPc region and BP region, respectively. Location of target sequence designs are shown in FIG. 3. Four kinds of primers will be designed based on the six primer regions designed in this way. LAMP amplification using these primers will provide portions of LAMP amplification products as shown in FIG. 4. In these LAMP amplification products, target sequence regions; FPc region, FP region, BP region and BPc region will be located in a single-stranded loop of amplified products. Since F1 region and F1c region, and B1 region and B1c region have complementary sequences from the beginning, they will self-hybridize with each other to give double strands. In this case, F2c region, F2 region, B1c region and B1 region will be located in loop regions of single strands as shown in FIG. 4. These regions, F2c region, F2 region, B1c region and B1c region, may overlap, in part, with target sequence regions FPc region, FP region, BPc region and BP region. Since some target sequences included in amplification products are single-stranded as shown in FIG. 4, they can be detected, without any denaturation procedure, by specific hybridization with probe nucleic acids FP, FPc, BP and BPc that are complement to each target sequences as shown in FIG. 4. As used herein, specific hybridization means that it can detect minor differences when Single Nucleotide Polymorphisms (SNPs) or mutations occur.

<Probe Nucleic Acids>

As explained in FIG. 4 according to the present invention, target sequences included in single-stranded loop structures of stem-and-loop structured nucleic acids for measurement are detected by means of probe nucleic acids having sequences complementary thereto. These probe nucleic acids are immobilized onto a solid substrate surface. Probes are used typically comprising a part of a DNA chip.

A DNA chip is a several-centimeter-square of glass or silicon substrate onto which several tens to several hundred thousand kinds probes with different sequences are immobilized. DNA chips allow for simultaneous investigation of information on multiple sequences. This enables analyses of gene expression patterns and SNPs to be completed in several days, which required several weeks previously. Currently, DNA chips are mainly used in search for new genes, elucidation of functions and techniques for supporting researches, but recently, they are becoming common techniques for disease diagnosis.

As an exemplary DNA chip, a technique of AFFYMETRIX are well known (see, for example, Proc. Natl. Acad. Sci. USA 91, 1994, p 5022-5026). In this technique, fluorescently-labeled sample genes are reacted with probes on a chip and detected by means of a high-sensitive fluorescent analysis apparatus. Another type of a detection method developed is a current detection type DNA chip. In this method, intercalators specifically reactive with double-stranded DNA are added and electrochemical signals generated by the intercalators are measured. Electrical DNA chips are expected to be a promising second-generation DNA chip, because they need no labeling and expensive detection apparatuses (see, for example, Japanese Patent Publication H05-199898).

<Hybridization Reaction between Nucleic Acids for Measurement and Probes>

Figure 6A:
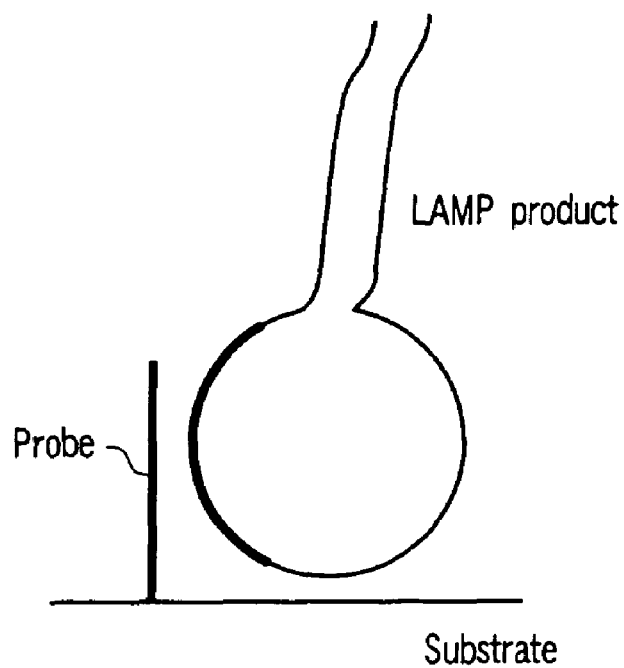
FIG. 6 schematically illustrates hybridization reaction between nucleic acid probe and a LAMP product in which a target sequence is located in its looped single stranded portion. While, in FIG. 6A, the double-stranded portion in the LAMP product extends away form the substrate plate, in FIG. 6B, the double-stranded portion extends toward the substrate plate.

The nucleic acids for measurement are bound to the solid surface via specific hybridization reaction between single-stranded target sequence located therein and the probe nucleic acids. In this invention, it is an additional characteristics that 5' to 3' sequence orientations of both the probe nucleic acid and the target sequence portion are arranged so that the double-stranded portion of the nucleic acid for measurement extends away from the solid surface when the probe nucleic acid and the target sequence portion are hybridized (see FIG. 5A). Such characteristics have been found based on a finding that if 5' to 3' sequence orientations of both the probe nucleic acid and the target sequence portion are arranged as shown in FIG. 5C, complex conformations characteristics to LAMP products cause steric hindrance together with a probe-bound substrate (see FIG. 6B) and this causes reduction in hybridization efficiency. Steric hindrance produced by LAMP products and a solid substrate on which probe nucleic acids are bound can be avoided (see FIG. 6A) by arranging 5' to 3' sequence orientations of both the probe nucleic acid and the target sequence portion so that the double-stranded portion of the nucleic acid for measurement extends away from the solid surface when the probe nucleic acid and the target sequence portion are hybridized (see FIG. 5B), thereby achieving improvement in hybridization efficiency.

<Detection of Nucleic Acids for Measurement Hybridized to Probe Nucleic Acids>

In this invention, when detecting presence or absence of the nucleic acids for measurement hybridized to probe nucleic acids, detection means is not limited to particular means in any way. For example, detection can be made based on fluorescent labels or by means of electrical detection using a double-strand specific intercalator generating electrical potential

EXAMPLE 1

A method for nucleic acid detection according to an embodiment of the present invention will now be described more specifically by way of the Examples.

In this example, LAMP amplification products are produced as a sample nucleic acid and target nucleic acid(s) present in the LAMP amplification products were detected in an electrical current system after hybridization reaction. For LAMP reaction, two sets of the following primers were used and a part of N-Acetyltransferase 2 (NAT2) gene were amplified (1) Synthetic Oligonucleotide Primer 1

Figure 7:
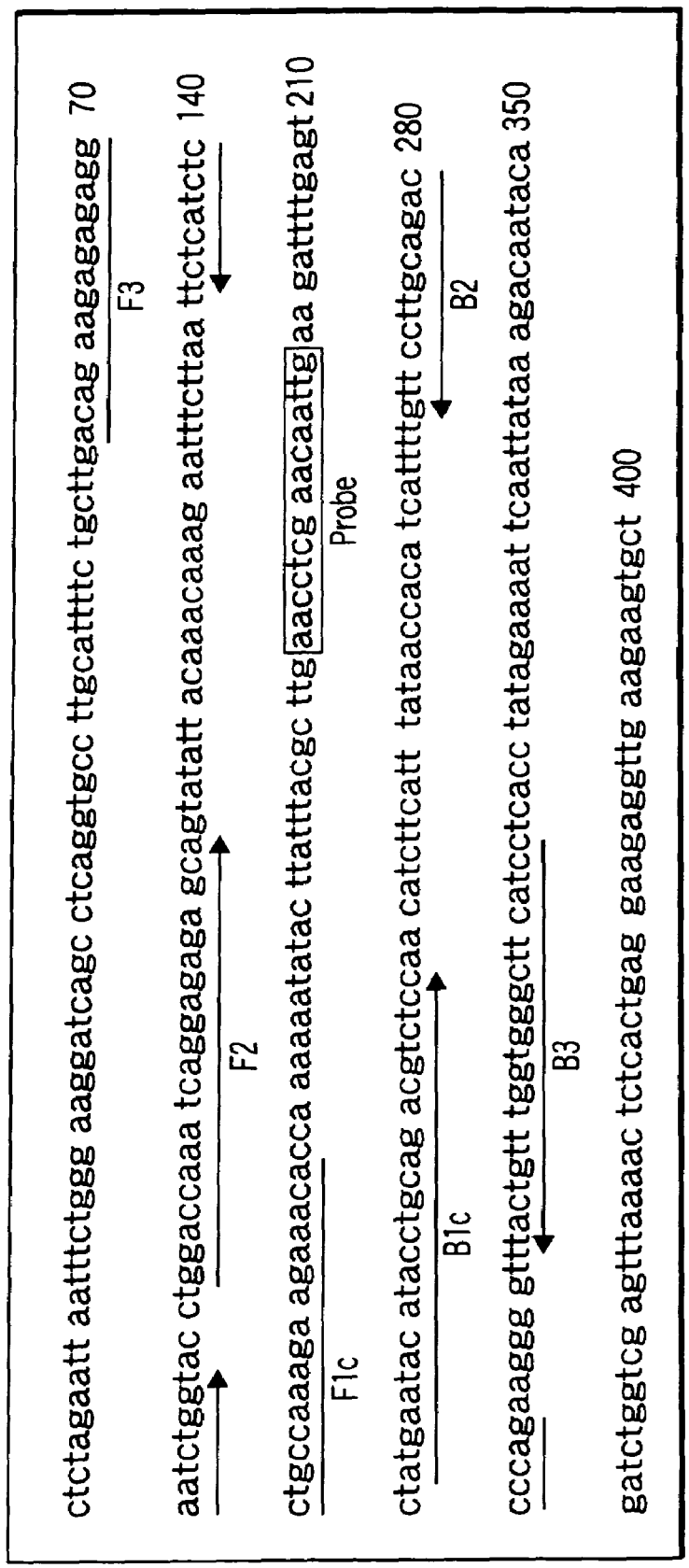
FIG. 7 shows a primer which is designed to have a target nucleic acid in a double-stranded region (stem region) as well as the position of a target sequence in NAT2 gene.

Target nucleic acid sequences were designed to be located in a double-stranded region (stem region) of the LAMP amplification products. Peripheral genomic sequences are shown in FIG. 7 (SEQ ID NO: 15).

```
NAT F3 Primer:    5' ACAGAAGAGAGAGGAATCTGGT 3'
                  (SEQ ID NO: 1)

NAT FIP Primer:   5' TGTTTCTTCTTTGGCAGGAGATGAGAA-GGACCAAATCAGGAGAGAGCA 3'
                  (SEQ ID NO: 2)

NAT B3 Primer:    5' GATGAAGCCCACCAAACAGTA 3'
                  (SEQ ID NO: 3)

NAT BIP Primer:   5' ATGAATACATACAGACGTCTCCCTGGGGTCTGCAAGGAAC 3'
                  (SEQ ID NO: 4)
```

Primer 2

Figure 8:
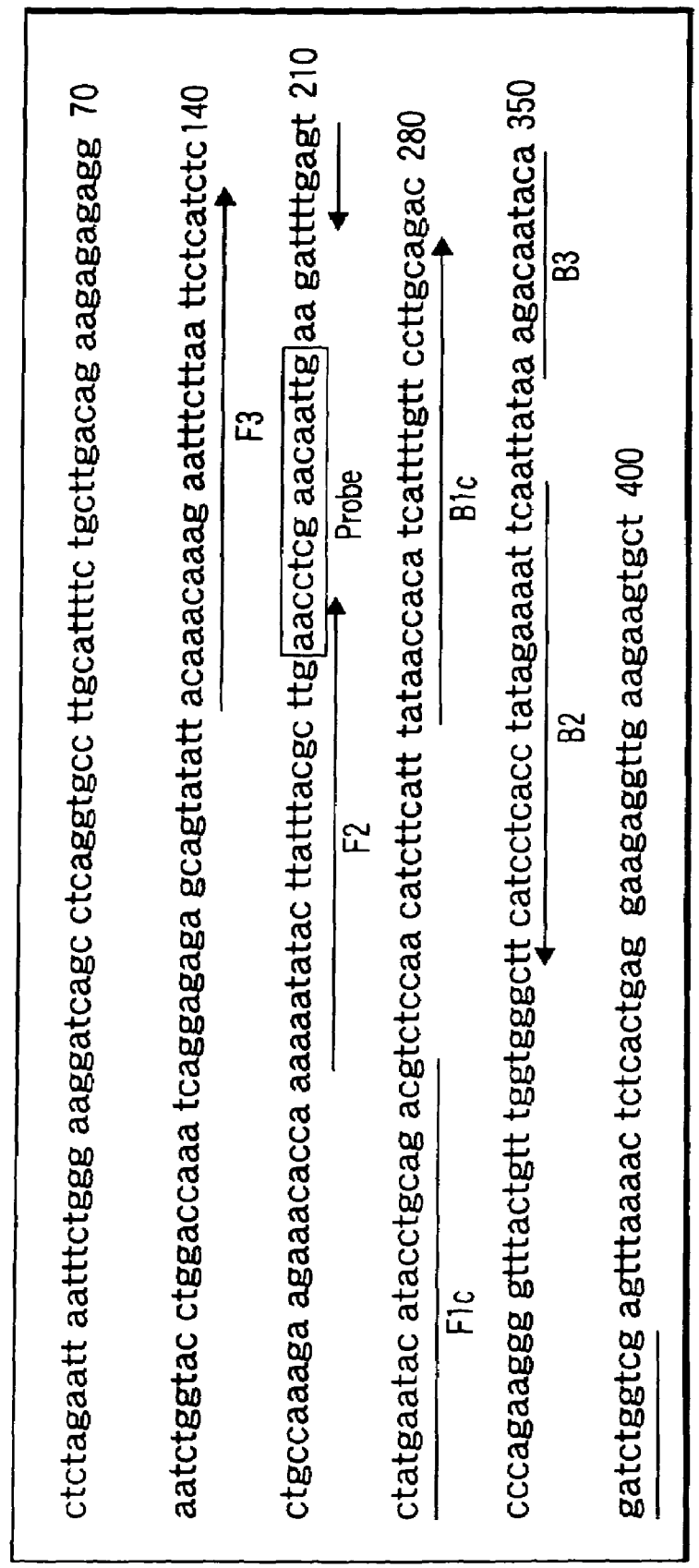
FIG. 8 shows a primer which is designed to have a target nucleic acid in a single-stranded region (loop region) as well as the position of a target sequence in NAT2 gene.

Target nucleic acid sequences were designed to be located in a single-stranded region (loop region) of the LAMP amplification products. Peripheral genomic sequences are shown in FIG. 8 (SEQ ID NO: 15)

```
NAT F3 Primer:    5' ACAAACAAAGAATTTCTTAATTCTCAT 3'
                  (SEQ ID NO: 5)

NAT FIP Primer:   5' CGTCTGCAGGTATGTATTCATAGACTCAAAAAATATACTTATTTACGCTTGAACC 3'
                  (SEQ ID NO: 6)

NAT B3 Primer:    5' CGACCAGATCTGTATTGTCTT 3'
                  (SEQ ID NO: 7)

NAT BIP Primer:   5' ATAACCACATCATTTTGTTCCTTGCATGAATTTTCTATAGGTGAGGATGA 3'
                  (SEQ ID NO: 8)
```

(2) LAMP Reaction Solution

The composition of the LAMP reaction solution was as follows:

| Sterile ultrapure water | 1.5 µL |
|---|---|
| Bst DNA polymerase | 1 µL |
| buffer | 12.5 µL |
| buffer components | |
| Tris HCl (pH 8.0) | 40 mM |
| KCl | 20 mM |
| $MgSO_4$ | 16 mM |
| $(NH_4)_2SO_4$ | 20 mM |
| Tween 20 | 0.2% |
| Betaine | 1.6 M |
| dNTP | 2.8 mM |
| F3-primer (10 µM) | 0.5 µL |
| B3-primer (10 µM) | 0.5 µL |
| FIP-primer (10 µM) | 4 µL |
| BIP-primer (10 µM) | 4 µL |
| Template (purified human genome) | 1 µL |
| Total | 25 µL |

(3) Nucleic Acid Amplification by LAMP Method

Nucleic acid amplification was performed at 58° C. for one hour. For negative control, sterile water was added instead of templates.

(4) Confirmation of Nucleic Acid Amplification

LAMP products amplified by the methods described above were confirmed by agarose-gel electrophoresis as shown in FIG. 9. The presence or absence of products of interest were confirmed by restriction enzyme cleavage. In FIG. 9, lanes 1-7 correspond to the following samples 1-7, respectively.

Electrophoretic results are shown below.

1. 100 bP ladder (TAKARA)
2. Negative control: a target nucleic acid is located in a double-stranded region
3. Positive control: a target nucleic acid is located in a double-stranded region
4. Negative control: a target nucleic acid is located in a single-stranded region
5. Positive control: a target nucleic acid is located in a single-stranded region
6. Pst I restriction enzyme treated: a target nucleic acid is located in a double-stranded region
7. Pst I restriction enzyme treated: a target nucleic acid is located in a single-stranded region Digestion with a restriction enzyme gave fragments as expected by theory. This indicates these LAMP products are specific amplification products.

(5) Preparation of Nucleic Acid Probe Immobilized Electrodes

Nucleotide sequences of nucleic acid probes are shown below.

Positive-probe FP: AACCTCGAACAATTG (SEQ ID NO: 9) 3' SH, 5' SH probes total of two Positive-prove FPc: CAATTGTTCGAGGTT (SEQ ID NO: 10) 3' SH, 5' SH probes total of two N-probe NP: CTGGACGAAGACTGA (SEQ ID NO: 11)

FP probe and FPc probe are complementary to each other. A total of four 3' SH and 5' SH modified probes were tested for FP probe and FPc probe. In contrast, N-probe served as negative control and had sequences unrelated to four probes described above.

Figure 10:
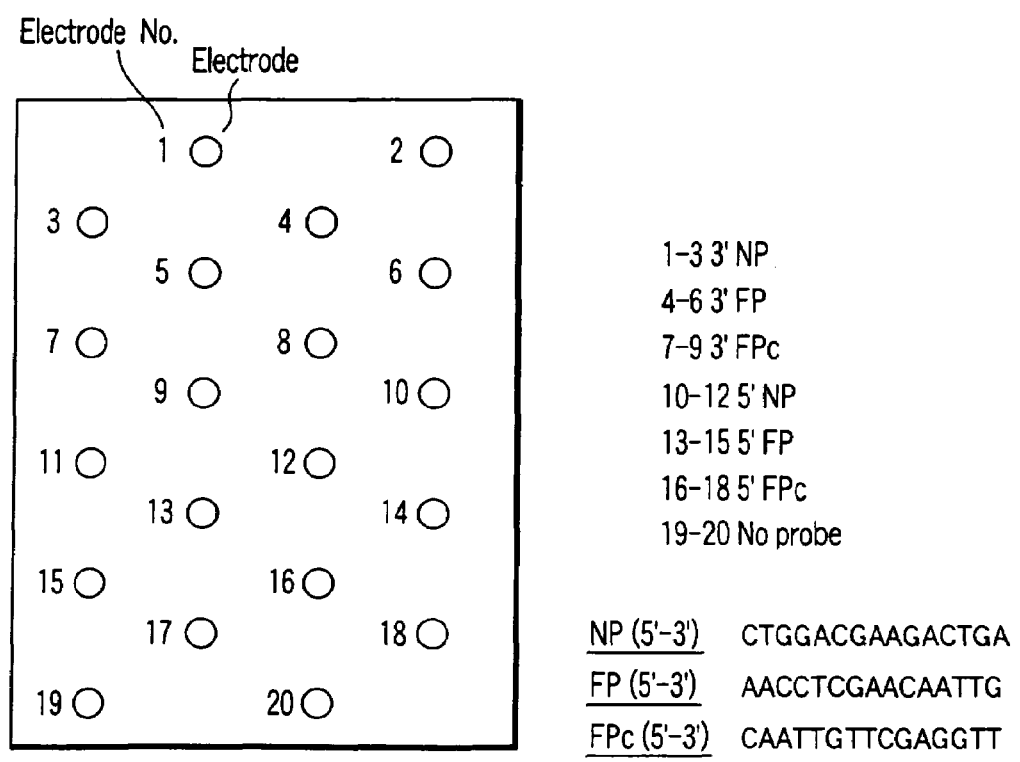
FIG. 10 shows an arrangement of electrodes used in the Examples to detect LAMP products.

Probe solution containing the labeled probes was spotted onto gold electrodes and, after standing one hour, the electrodes were immersed in mercaptohexanol solution and washed 0.2×SSC solution. The electrode were then washed with ultrapure water, air-dried and used as probe-immobilized electrodes. Arrangement of electrodes is as shown in FIG. 10.

(6) Hybridization of LAMP Products to Nucleic Acid Probes

LAMP products amplified in the step (3) above were used as sample nucleic acids. The surface prepared in step (4) on which nucleic acid probes were immobilized was immersed in LAMP products added by 2×SSC salt, hybridization reaction was performed by standing at 35° C. The probe-immobilized surface was quickly washed with ultra pure water. The electrodes were immersed for 15 minutes in phosphate buffer containing 50 µM Hoechst 33258 solution (an intercalator) and oxidation current response of Hoechst 33258 molecule was measured.

(7) Results

Figure 11A:
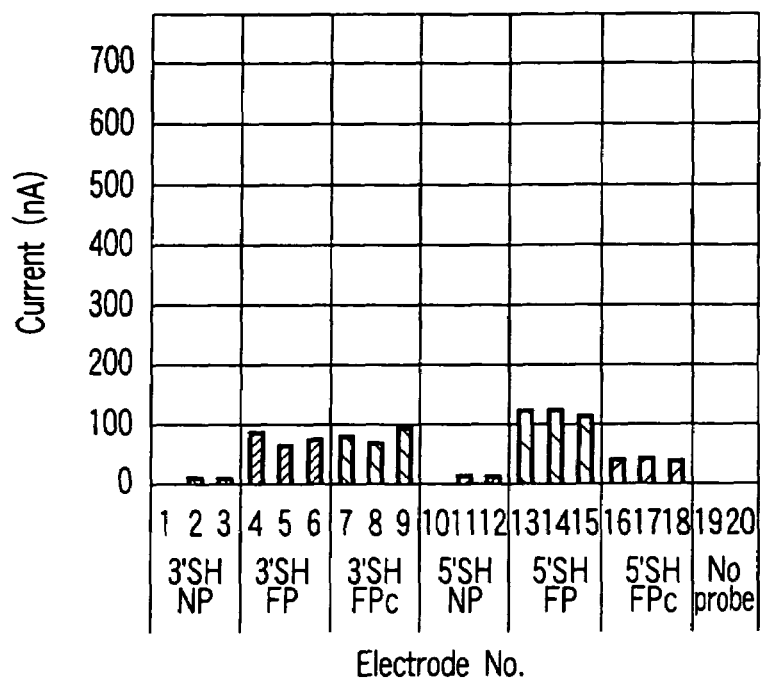
FIG. 11A is a graph showing measurement results obtained from LAMP products having a target nucleic acid in its double-stranded portion.
Figure 11B:
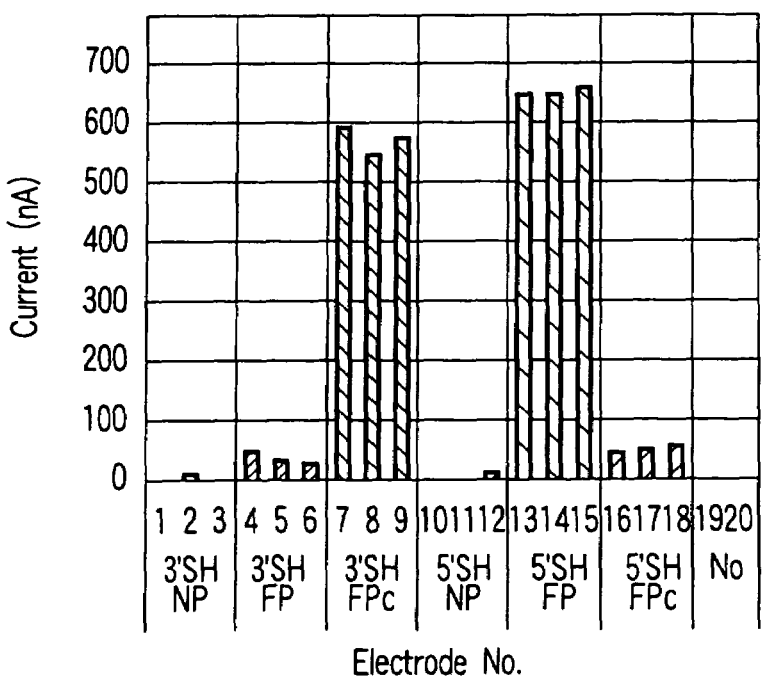
FIG. 11B is a graph showing measurement results obtained from LAMP products having a target nucleic acid in a looped single-stranded portion.

In FIG. 11, the results of electrical current measurements were shown as an increment of current values generated in electrodes on which each probes were immobilized. In LAMP products in which target sequences are located in a double-stranded portion (stem portion), no increment in current values derived from hybridization was found for NP, 3' SH FP, 3' SH FPc, 5' SH FP and 5' SH FPc (FIG. 11A). In contrast, in LAMP products in which target nucleic acid is located in a single-stranded loop portion, no increment in current values derived from hybridization was found for NP, 3' SH FP and 5' SH FP, but increment in current value probably derived from hybridization was found for 3' SH FPc and 5' SH FP (FIG. 11B).

Figure 6B:
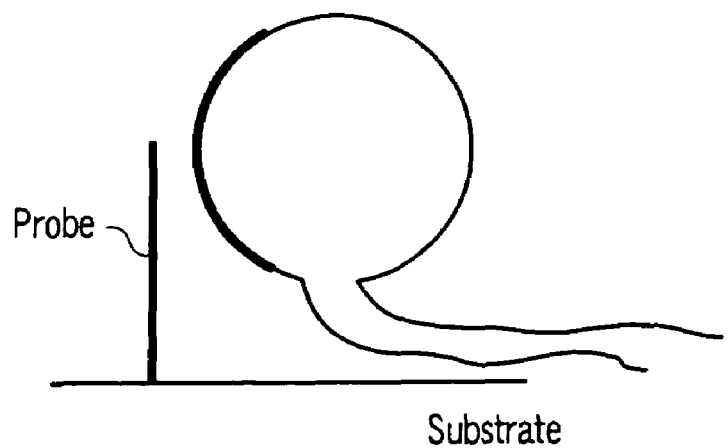

For 3' SH FP and 5' SH FPc, which gave no current signal values increase when used with products having target nucleic acid located in a single-stranded loop portion, the double-stranded portion in LAMP products, upon hybridization with the single-stranded loop portion of LAMP products, extended toward the substrate thereby causing steric hindrance (see FIG. 5C and FIG. 6B). In contrast, for 3' SH FPc and 5' SH FP, which gave current signal value increase, the double-stranded portion in LAMP products extends away from the substrate thereby streic hindrance is avoided (see FIG. 5B and FIG. 6A).

It was found, from these results, that it was essential to locate target nucleic acids in looped single-stranded portions to detect LAMP products with DNA chips. It was also found that 5' to 3' sequence orientations of both the probe nucleic acid and the target sequence portion must be arranged so that the double-stranded portion of LAMP products extended away from the solid surface in order to avoid steric hindrance occurred between LAMP products and substrates upon hybridization reaction.

EXAMPLE 2

By way of an application of a nucleic acid detection method according to this invention, single nucleotide polymorphisms (SNPs) in target nucleic acid sequences were detected.

In Example 2, LAMP products were prepared for sample nucleic acids as described in Example 1. After hybridization, SNPs in the target nucleic acid sequences in the LAMP products were detected in a electrical current detection system.

(1) LAMP Products Used for Detection

LAMP products used were same as those amplified by Primer 2 described in Example 1, (1) Synthetic oligonucleotide.

(2) Probes used for detection

Nucleotide sequences of the nucleic acid probes are shown below

```
Positive-probe FPc: CAATTGTTCGAGGTT 3'SH (a
probe used in Example 1)
(SEQ ID NO: 10)

Positive-probe FPc SNP: CAATTGTTGGAGGTT 3' SH
(SEQ ID NO: 12)

Positive-probe FPc 25mer:
ATCTTCAATTGTTCGAGGTTCAAGC 3' SH
(SEQ ID NO: 13)

Positive-probe FPc 25mer SNP:
ATCTTCAATTGTTGGAGGTTCAAGC 3' SH
(SEQ ID NO: 14)

N-probe NP: CTGGACGAAGACTGA 3' SH
(SEQ ID NO: 11)
```

FPc and NP were same as those used in Example 1. For FPc SNP, G near the center of FPc sequence was changed into C. FPc 25 mer was a target nucleic acid sequence having five base extensions in both upstream and downstream of FPc. For FPc 25 mer SNP, G near the center of FPc 25 mer sequence was changed into C. All five probes above were 3' SH modified.

Figure 12:
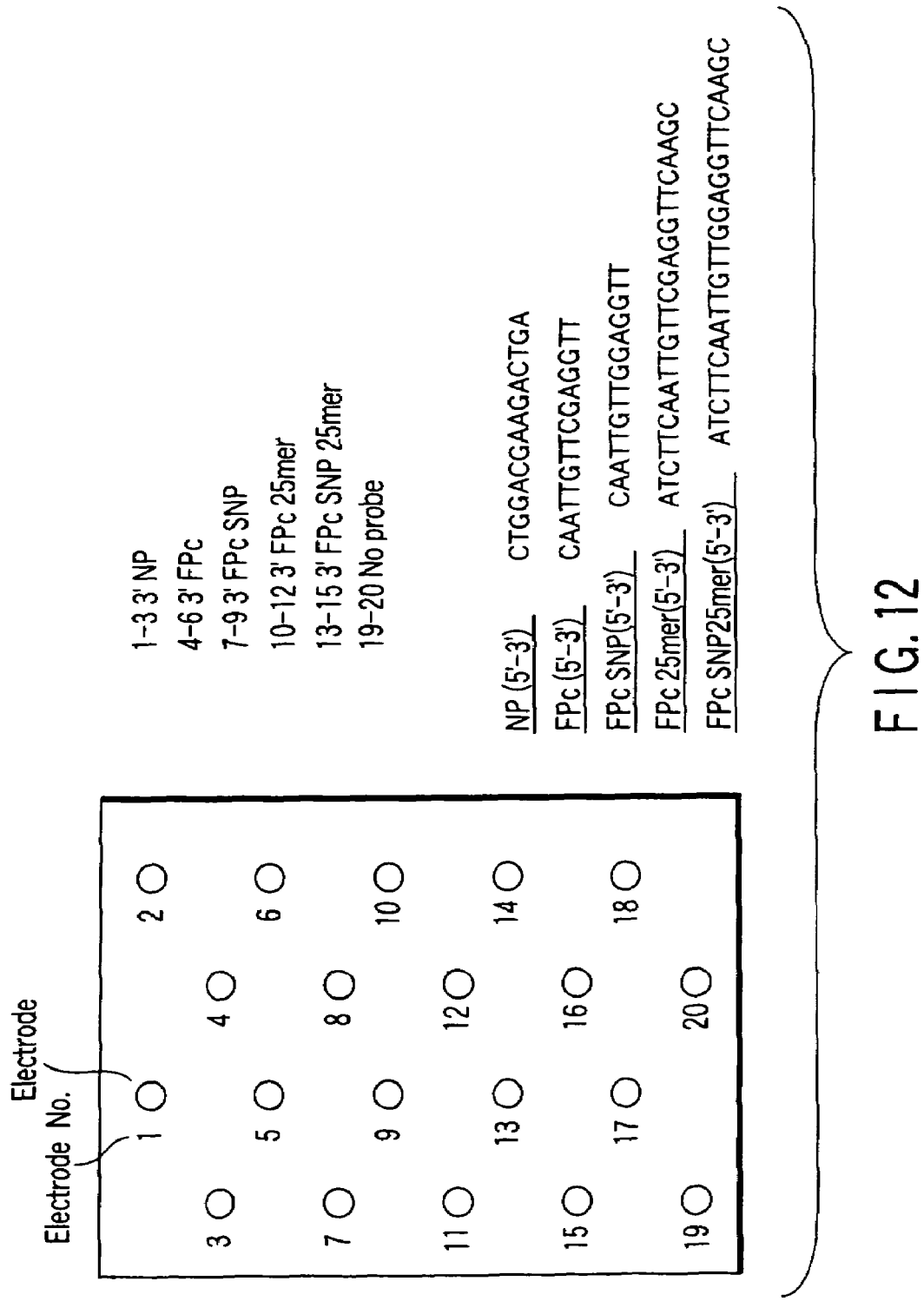
FIG. 12 illustrates an arrangement of electrodes used in the Example 2 to detect SNPs in LAMP products.

Probes were immobilized in the same manner as described in the Example 1. Arrangement of electrodes is shown in FIG. 12.

(3) Hybridization of LAMP Products to Nucleic Acids

LAMP products amplified in the above step (1) were used as sample nucleic acids. The surface prepared in step (2) on which nucleic acid probes were immobilized was immersed in LAMP products added by 2×SSC salt, and by standing for 60 minutes at 35° C., hybridization reaction was performed. The substrates washed under four different conditions were made: immersed in 0.2×SSC buffer at 35° C., 40° C. or 45° C. for 40 minutes followed by quick wash with ultra pure water; or just quickly washed with ultrapure water after hybridization. The electrodes were immersed for 15 minutes in phosphate buffer containing 50 μM Hoechst 33258 solution (an intercalator) and oxidation current response of Hoechst 33258 molecule was measured.

(4) Results

Figure 13A:
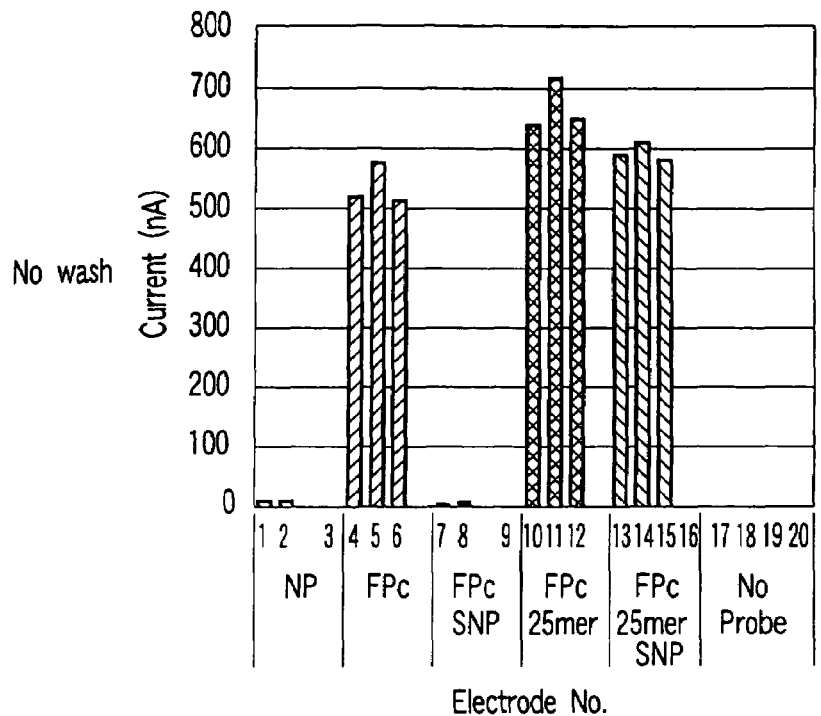
FIG. 13A is a graph showing measurement results obtained from substrate plates washed quickly with ultrapure water after hydridization.
Figure 13B:
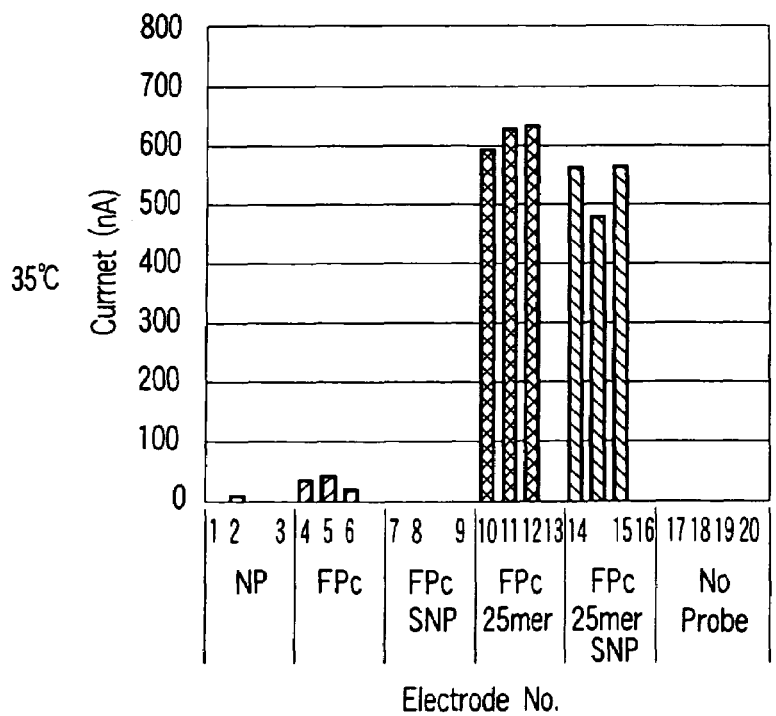
FIG. 13B is a graph showing measurement results obtained from substrate plates immersed in washing buffer at 35° C. for 40 minutes after hybridization.

In FIG. 13, the results of electrical current measurements were shown as an increment of electrical current generated in electrodes on which each probes had been immobilized. Regarding the FPc and FPcSNP, (A) there was no increase in electrical current values for FPcSNP when used with a substrate quickly washed with ultrapure water after hybridization, on the contrary, significant increase in electrical current values was observed for FPc. In addition, (B) increase in electrical current values was disappeared for both FPc and FPc SNP when used with substrates that had been washed with 0.2×SSC solution at 35° C. for 40 minutes after hybridization. This indicates FPc and FPc SNP can identify SNPs under the washing condition (A).

Regarding extended target sequences, FPc 25 mer and FPc 25 mer SNP, (C) increase in electrical current values was found for both FPc 25 mer and FPc 25 mer SNPs when used with substrates that had been washed with 0.2×SSC solution at 40° C. for 40 minutes after hybridization. In contrast, (D) when substrates had been washed with 0.2×SSC solution at 45° C. for 40 minutes after hybridization, no increase in electrical current values was found for FPc 25 mer SNP, but significant increase was found for FPc 25 mer. This indicates FPc 25 mer and FPc 25 mer SNP can identify SNPs under the washing condition (D).

These results show that SNPs can be detected by selecting appropriate hybridization or washing conditions depending on different probe sequences, or by selecting optimal probes for defined hybridization and washing condition.

This invention shall never be limited to the embodiments specifically described above and, in practicing this invention, constituent elements thereof can be modified to give other embodiments without departing from the spirit or scope of the invention. In addition, various inventions will be given by combining multiple constituent elements disclosed in the embodiment stated above. For example, among all constituent elements mentioned in the embodiments, some constituent elements could be omitted. Furthermore, constituents elements of different embodiments could appropriately combined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of detecting a target nucleic acid sequence comprising:

providing a stem-and-loop structured nucleic acid for measurement wherein the nucleic acid comprises complementary sequence portions located at both terminals and a target sequence portion therebetween as well as a double-stranded portion formed by hybridization of the complementary sequence portions located at both terminals and a remaining looped single-stranded portion;

providing a probe nucleic acid having a sequence complementary to the target sequence portion wherein one end of the probe nucleic acid being immobilized to a solid substrate surface;

reacting the nucleic acid for measurement with the probe nucleic acid to specifically hybridize the target sequence portion of the nucleic acid for measurement to the probe nucleic acid; and detecting presence or absence of the nucleic acid for measurement hybridized to the probe nucleic acid by using a double strand specific intercalator, thereby detecting the target nucleic acid sequence.

2. A method according to claim 1, wherein 5' to 3' sequence orientations of both the probe nucleic acid and the target sequence portion are arranged so that the double-stranded portion of the nucleic acid for measurement extends away from the solid surface when the probe nucleic acid and the target sequence portion is hybridized.

3. A method according to claim 1, wherein the nucleic acid for measurement and the probe nucleic acid are DNA.

4. A method according to claim 2, wherein the nucleic acid for measurement and the probe nucleic acid are DNA.

5. A method according to claim 1, wherein the probe nucleic acid is a component of a DNA chip.

6. A method according to claim 2, wherein the probe nucleic acid is a component of a DNA chip.

7. A method according to claim 1, wherein the nucleic acid for measurement is a LAMP product amplified by LAMP method, wherein the LAMP product comprises at least one part selected from the group consisting of a first part, a second part, a third part, and a fourth part of the LAMP product; the first part of the LAMP product comprising F1c, F2c, and F1 arranged in this order, the second part of the LAMP product comprising F1c, F2, and F1 arranged in this order, the third part of the LAMP product comprising B1c, B2c, and B1 arranged in this order, and the fourth part of the LAMP product comprising B1c, B2, and B1 arranged in this order.

8. A method according to claim 2, wherein the nucleic acid for measurement is a LAMP product amplified by LAMP method, wherein the LAMP product comprises at least one part selected from the group consisting of a first part, a second part, a third part, and a fourth part of the LAMP product; the first part of the LAMP product comprising F1c, F2c, and F1 arranged in this order, the second part of the LAMP product comprising F1c, F2 and F1 arranged in this order, the third part of the LAMP product comprising B1c, B2c, and B1 arranged in this order, and the fourth part of the LAMP product comprising B1c, B2, and B1 arranged in this order.

9. A method according to claim 7, wherein the target sequence in the LAMP product is inserted between F1 region and F2 region, between F2c region and F1c region, between B1 region and B2 region, and/or between B2c region and B1c region of the LAMP product.

10. A method according to claim 8, wherein the target sequence in the LAMP product is inserted between F1 region and F2 region, between F2c region and F1c region, between B1 region and B2 region, and/or between B2c region and B1c region of the LAMP product.

11. A method according to claim 9, wherein a part of the target sequence overlaps with a part of the sequence of the F2 region, F2c region, B2 region, and/or B2c region of the LAMP product.

12. A method according to claim 10, wherein a part of the target sequence overlaps with a part of the sequence of F2 region, F2c region, B2 region, and/or B2c region of the LAMP product.

13. A method according to claim 1, wherein the presence or absence of the nucleic acid for measurement hybridized to the probe nucleic acid is detected electrically using a double-strand specific intercalator.

14. A method according to claim 2, wherein the presence or absence of the nucleic acid for measurement hybridized to the probe nucleic acid is detected electrically using a double-strand specific intercalator.

* * * * *